US012558474B2

(12) United States Patent (10) Patent No.: US 12,558,474 B2

Cheng et al. (45) Date of Patent: *Feb. 24, 2026

(54) DYNAMIC PRESSURE RESPONSE SYSTEM

(71) Applicant: C. R. Bard, Inc., Franklin Lakes, NJ (US)

(72) Inventors: Jason Jishen Cheng, Avondale Estates, GA (US); David M. Simiele, Roswell, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 242 days.

This patent is subject to a terminal disclaimer.

(21) Appl. No.: 18/036,335

(22) PCT Filed: Nov. 19, 2020

(86) PCT No.: PCT/US2020/061367

§ 371 (c)(1),
(2) Date: May 10, 2023

(87) PCT Pub. No.: WO2022/108589

PCT Pub. Date: May 27, 2022

(65) Prior Publication Data

US 2024/0042120 A1 Feb. 8, 2024

(51) Int. Cl.
*A61M 1/00* (2006.01)
*A61M 25/00* (2006.01)
(Continued)

(52) U.S. Cl.
CPC .......... *A61M 1/85* (2021.05); *A61M 25/0017* (2013.01); *A61M 2039/226* (2013.01);
(Continued)

(58) Field of Classification Search
CPC ................ A61M 1/85; A61M 25/0017; A61M 2039/226; A61M 2202/0496; A61M 2205/3331; A61M 2205/50; G16H 40/63
See application file for complete search history.

(56) References Cited

U.S. PATENT DOCUMENTS 3,661,143 A 5/1972 Henkin
3,781,920 A 1/1974 Browne et al.
(Continued)

FOREIGN PATENT DOCUMENTS

CA 2882654 A1 10/2007
CN 2445749 Y 9/2001
(Continued)

OTHER PUBLICATIONS

EP 23188337.2 filed May 21, 2019 Extended European Search Report dated Dec. 4, 2023.
(Continued)

*Primary Examiner* — Philip R Wiest
(74) *Attorney, Agent, or Firm* — Rutan & Tucker LLP

(57) ABSTRACT

Embodiments disclosed herein are directed to a dynamic pressure response system for fully automated clearing of dependent loops from a fluid drainage system. Fluid drainage systems include a flexible drainage tube providing fluid communication with a collection container. Dependent loops can form within the tube leading to pooling of urine and provide an increased risk in CAUTI. Dynamic pressure response systems can automatically detect the presence of dependent loops and provide a low-rate positive air pressure to clear the columnized fluid. Further, the system can automatically detect mixed fluid states when a noise level of pressure signals increases, the system can then provide high-rate positive air pressure to clear mixed fluid state liquid from the tube lumen.

20 Claims, 3 Drawing Sheets

(51) Int. Cl.
    *A61M 39/22*           (2006.01)
    *G16H 40/63*           (2018.01)
(52) U.S. Cl.
    CPC .............. *A61M 2202/0496* (2013.01); *A61M 2205/3331* (2013.01); *A61M 2205/50* (2013.01); *G16H 40/63* (2018.01)

(56) References Cited

U.S. PATENT DOCUMENTS

| | | |
|---|---|---|
| 3,851,650 A | 12/1974 | Darling |
| 3,919,455 A | 11/1975 | Sigdell et al. |
| 4,276,889 A | 7/1981 | Kuntz et al. |
| 4,286,590 A | 9/1981 | Murase |
| 4,291,692 A | 9/1981 | Bowman et al. |
| 4,296,749 A | 10/1981 | Pontifex |
| 4,305,405 A | 12/1981 | Meisch |
| 4,312,352 A | 1/1982 | Meisch et al. |
| 4,343,316 A * | 8/1982 | Jespersen ............ G01F 23/2921 |
| | | 600/580 |
| 4,443,219 A | 4/1984 | Meisch et al. |
| 4,448,207 A | 5/1984 | Parrish |
| 4,509,366 A | 4/1985 | Matsushita et al. |
| 4,532,936 A | 8/1985 | LeVeen et al. |
| 4,658,834 A | 4/1987 | Blankenship et al. |
| 4,712,567 A | 12/1987 | Gille et al. |
| 4,723,950 A | 2/1988 | Lee |
| 4,834,706 A | 5/1989 | Beck et al. |
| 4,850,375 A | 7/1989 | Rosenberg |
| 4,889,532 A | 12/1989 | Metz et al. |
| 5,002,541 A | 3/1991 | Conkling et al. |
| 5,146,637 A | 9/1992 | Bressler et al. |
| 5,409,014 A | 4/1995 | Napoli et al. |
| 5,586,085 A | 12/1996 | Lichte |
| 5,725,515 A | 3/1998 | Propp |
| 5,733,319 A | 3/1998 | Neilson et al. |
| 5,738,656 A | 4/1998 | Wagner |
| 5,747,824 A | 5/1998 | Jung et al. |
| 5,769,087 A | 6/1998 | Westphal et al. |
| 5,807,278 A | 9/1998 | McRae |
| 5,823,972 A | 10/1998 | McRae |
| 5,891,051 A | 4/1999 | Han et al. |
| 5,911,786 A | 6/1999 | Nielsen et al. |
| 6,129,684 A | 10/2000 | Sippel et al. |
| 6,132,407 A | 10/2000 | Genese et al. |
| 6,250,152 B1 | 6/2001 | Klein et al. |
| 6,256,532 B1 | 7/2001 | Cha |
| 6,261,254 B1 | 7/2001 | Baron et al. |
| 6,434,418 B1 | 8/2002 | Neal et al. |
| 6,579,247 B1 | 6/2003 | Abramovitch et al. |
| 6,592,612 B1 | 7/2003 | Samson et al. |
| 6,709,420 B1 | 3/2004 | Lincoln et al. |
| 6,716,200 B2 | 4/2004 | Bracken et al. |
| 7,011,634 B2 | 3/2006 | Paasch et al. |
| 7,161,484 B2 | 1/2007 | Tsoukalis |
| 7,211,037 B2 | 5/2007 | Briggs et al. |
| 7,437,945 B1 | 10/2008 | Feller |
| 7,442,754 B2 | 10/2008 | Tepper et al. |
| 7,739,907 B2 | 6/2010 | Boiarski |
| 7,871,385 B2 | 1/2011 | Levinson |
| 7,931,630 B2 | 4/2011 | Nishtala et al. |
| 7,976,533 B2 | 7/2011 | Larsson |
| 7,998,126 B1 | 8/2011 | Fernandez |
| 8,295,933 B2 | 10/2012 | Gerber et al. |
| 8,328,733 B2 | 12/2012 | Forte et al. |
| 8,328,734 B2 | 12/2012 | Salvadori et al. |
| 8,337,476 B2 | 12/2012 | Greenwald et al. |
| 8,374,688 B2 | 2/2013 | Libbus et al. |
| 8,403,884 B2 | 3/2013 | Nishtala |
| 8,471,231 B2 | 6/2013 | Paz |
| 8,663,128 B2 | 3/2014 | Paz et al. |
| 8,773,259 B2 | 7/2014 | Judy et al. |
| 8,790,277 B2 | 7/2014 | Elliott et al. |
| 8,790,320 B2 | 7/2014 | Christensen |
| 8,790,577 B2 | 7/2014 | Mizumoto et al. |
| 8,813,551 B2 | 8/2014 | Boiarski |
| 8,827,924 B2 | 9/2014 | Paz et al. |
| 8,832,558 B2 | 9/2014 | Cardarelli et al. |
| 8,900,196 B2 | 12/2014 | Andino |
| 9,045,887 B2 | 6/2015 | O'Malley |
| 9,050,046 B2 | 6/2015 | Elliott et al. |
| 9,074,920 B2 | 7/2015 | Mendels et al. |
| 9,216,242 B2 | 12/2015 | Nishtala et al. |
| 9,480,821 B2 | 11/2016 | Ciccone et al. |
| 9,592,034 B2 | 3/2017 | Hall et al. |
| 9,642,987 B2 | 5/2017 | Bierman et al. |
| 9,731,097 B2 | 8/2017 | Andino et al. |
| 9,895,095 B2 | 2/2018 | Chen |
| 9,928,341 B2 | 3/2018 | Angelides |
| 9,962,516 B2 | 5/2018 | Lampotang et al. |
| 10,071,202 B2 | 9/2018 | Handler |
| 10,182,747 B2 | 1/2019 | Charlez et al. |
| 10,245,008 B2 | 4/2019 | Paige |
| 10,301,807 B1 | 5/2019 | Kolesar |
| 10,362,981 B2 | 7/2019 | Paz et al. |
| 10,383,606 B1 | 8/2019 | McCord et al. |
| 10,448,875 B2 | 10/2019 | Holt et al. |
| 10,722,679 B2 | 7/2020 | Lampotang et al. |
| 10,799,386 B1 | 10/2020 | Harrison, Sr. |
| 10,881,320 B2 | 1/2021 | Duval et al. |
| 10,881,778 B2 | 1/2021 | Scarpaci et al. |
| 11,291,577 B2 | 4/2022 | Seres et al. |
| 11,473,958 B2 | 10/2022 | Holt et al. |
| 11,540,760 B1 | 1/2023 | Guillemette |
| 11,654,042 B2 | 5/2023 | Hughett, Sr. |
| 11,703,365 B2 | 7/2023 | Tourchak et al. |
| 12,083,261 B2 | 9/2024 | Justice et al. |
| 12,109,353 B2 * | 10/2024 | Cheng .............. A61M 25/0017 |
| 12,408,853 B2 | 9/2025 | Kriscovich et al. |
| 2001/0056226 A1 | 12/2001 | Zodnik et al. |
| 2002/0016719 A1 | 2/2002 | Nemeth et al. |
| 2002/0161314 A1 | 10/2002 | Sarajarvi |
| 2002/0193760 A1 | 12/2002 | Thompson |
| 2003/0000303 A1 | 1/2003 | Livingston et al. |
| 2003/0163183 A1 | 8/2003 | Carson |
| 2003/0163287 A1 | 8/2003 | Vock et al. |
| 2004/0267086 A1 | 12/2004 | Anstadt et al. |
| 2005/0020958 A1 | 1/2005 | Paolini et al. |
| 2005/0065583 A1 | 3/2005 | Voorhees et al. |
| 2005/0172712 A1 | 8/2005 | Nyce |
| 2005/0247121 A1 | 11/2005 | Pelster |
| 2006/0065713 A1 | 3/2006 | Kingery |
| 2006/0100743 A1 | 5/2006 | Townsend et al. |
| 2006/0253091 A1 | 11/2006 | Vernon |
| 2007/0010797 A1 | 1/2007 | Nishtala et al. |
| 2007/0078444 A1 * | 4/2007 | Larsson ................ A61M 1/743 |
| | | 604/540 |
| 2007/0106177 A1 | 5/2007 | Hama |
| 2007/0145137 A1 | 6/2007 | Mrowiec |
| 2007/0225668 A1 | 9/2007 | Otto |
| 2007/0252714 A1 | 11/2007 | Rondoni et al. |
| 2008/0027409 A1 | 1/2008 | Rudko et al. |
| 2008/0217391 A1 | 9/2008 | Roof et al. |
| 2008/0312550 A1 | 12/2008 | Nishtala et al. |
| 2008/0312556 A1 | 12/2008 | Dijkman |
| 2009/0056020 A1 | 3/2009 | Caminade et al. |
| 2009/0099629 A1 | 4/2009 | Carson et al. |
| 2009/0157430 A1 | 6/2009 | Rule et al. |
| 2009/0287170 A1 | 11/2009 | Otto |
| 2009/0315684 A1 | 12/2009 | Sacco et al. |
| 2010/0064426 A1 | 3/2010 | Chikara Imamura |
| 2010/0094204 A1 | 4/2010 | Nishtala |
| 2010/0130949 A1 | 5/2010 | Garcia |
| 2010/0137743 A1 | 6/2010 | Nishtala et al. |
| 2010/0262047 A1 | 10/2010 | Genis |
| 2011/0113540 A1 | 5/2011 | Plate et al. |
| 2011/0120219 A1 | 5/2011 | Barlesi et al. |
| 2011/0178425 A1 | 7/2011 | Nishtala et al. |
| 2011/0224636 A1 | 9/2011 | Keisic |
| 2011/0230824 A1 | 9/2011 | Salinas et al. |
| 2011/0238042 A1 | 9/2011 | Davis et al. |
| 2011/0251572 A1 | 10/2011 | Nishtala et al. |
| 2011/0263952 A1 | 10/2011 | Bergman et al. |
| 2012/0029408 A1 | 2/2012 | Beaudin |
| 2012/0035496 A1 | 2/2012 | Denison et al. |

(56) References Cited

U.S. PATENT DOCUMENTS

| 2012/0059286 A1 | 3/2012 | Hastings et al. |
| 2012/0078137 A1 | 3/2012 | Mendels et al. |
| 2012/0078235 A1 | 3/2012 | Martin et al. |
| 2012/0095304 A1 | 4/2012 | Biondi |
| 2012/0109008 A1 | 5/2012 | Charlez et al. |
| 2012/0118650 A1 | 5/2012 | Gill |
| 2012/0123233 A1 | 5/2012 | Cohen |
| 2012/0127103 A1 | 5/2012 | Qualey et al. |
| 2012/0226196 A1 | 9/2012 | DiMino et al. |
| 2012/0234434 A1 | 9/2012 | Woodruff et al. |
| 2012/0302917 A1 | 11/2012 | Fitzgerald et al. |
| 2012/0323144 A1* | 12/2012 | Coston .................... A61M 1/83 |
| | | 600/581 |
| 2012/0323502 A1 | 12/2012 | Tanoura et al. |
| 2013/0066166 A1 | 3/2013 | Burnett et al. |
| 2013/0109927 A1 | 5/2013 | Menzel |
| 2013/0109928 A1 | 5/2013 | Menzel |
| 2013/0131610 A1 | 5/2013 | Dewaele et al. |
| 2013/0218106 A1 | 8/2013 | Coston et al. |
| 2013/0245498 A1 | 9/2013 | Delaney et al. |
| 2013/0267871 A1 | 10/2013 | Delaney et al. |
| 2014/0039348 A1 | 2/2014 | Bullington et al. |
| 2014/0155781 A1 | 6/2014 | Bullington et al. |
| 2014/0155782 A1 | 6/2014 | Bullington et al. |
| 2014/0159921 A1 | 6/2014 | Qualey et al. |
| 2014/0187666 A1 | 7/2014 | Aizenberg et al. |
| 2014/0207085 A1 | 7/2014 | Brandt et al. |
| 2014/0243635 A1 | 8/2014 | Arefieg |
| 2014/0335490 A1 | 11/2014 | Baarman et al. |
| 2015/0120321 A1 | 4/2015 | David et al. |
| 2015/0233749 A1 | 8/2015 | Wang et al. |
| 2015/0342576 A1 | 12/2015 | Hall et al. |
| 2015/0343173 A1 | 12/2015 | Tobescu et al. |
| 2015/0359522 A1 | 12/2015 | Recht et al. |
| 2015/0362351 A1 | 12/2015 | Joshi et al. |
| 2016/0051176 A1 | 2/2016 | Ramos et al. |
| 2016/0051177 A1 | 2/2016 | Chen |
| 2016/0183819 A1 | 6/2016 | Burnett et al. |
| 2016/0374874 A1 | 12/2016 | Trepanier et al. |
| 2017/0035342 A1 | 2/2017 | Elia et al. |
| 2017/0043089 A1 | 2/2017 | Handler |
| 2017/0100068 A1 | 4/2017 | Kostov |
| 2017/0113000 A1 | 4/2017 | Tobescu et al. |
| 2017/0136209 A1 | 5/2017 | Burnett et al. |
| 2017/0140103 A1 | 5/2017 | Angelides |
| 2017/0196478 A1 | 7/2017 | Hunter |
| 2017/0202698 A1 | 7/2017 | Zani et al. |
| 2017/0249445 A1 | 8/2017 | Devries et al. |
| 2017/0290540 A1 | 10/2017 | Franco |
| 2017/0291012 A1 | 10/2017 | Iglesias |
| 2017/0307423 A1 | 10/2017 | Pahwa et al. |
| 2017/0322197 A1 | 11/2017 | Hall et al. |
| 2018/0015251 A1 | 1/2018 | Lampotang et al. |
| 2018/0110456 A1* | 4/2018 | Cooper .................. A61B 5/205 |
| 2018/0160961 A1 | 6/2018 | Gopinathan et al. |
| 2018/0214122 A1 | 8/2018 | Ansell et al. |
| 2018/0214297 A1 | 8/2018 | Hughett et al. |
| 2018/0245967 A1 | 8/2018 | Parker et al. |
| 2018/0280236 A1 | 10/2018 | Ludin et al. |
| 2018/0317891 A1 | 11/2018 | Kim |
| 2018/0344234 A1 | 12/2018 | McKinney et al. |
| 2019/0006047 A1 | 1/2019 | Gorek et al. |
| 2019/0017535 A1 | 1/2019 | Ormsbee et al. |
| 2019/0046102 A1 | 2/2019 | Kushnir et al. |
| 2019/0069829 A1 | 3/2019 | Bulut |
| 2019/0069830 A1 | 3/2019 | Holt et al. |
| 2019/0126006 A1* | 5/2019 | Rehm .................. A61M 39/22 |
| 2019/0150821 A1 | 5/2019 | Waters et al. |
| 2019/0167144 A1 | 6/2019 | Jung et al. |
| 2019/0201596 A1 | 7/2019 | Luxon et al. |
| 2019/0223844 A1 | 7/2019 | Aboagye et al. |
| 2019/0231244 A1 | 8/2019 | Swan et al. |
| 2019/0247236 A1 | 8/2019 | Sides et al. |
| 2019/0254582 A1 | 8/2019 | Wei et al. |
| 2019/0298317 A1 | 10/2019 | Colgan et al. |
| 2019/0321588 A1 | 10/2019 | Burnett et al. |
| 2019/0328945 A1 | 10/2019 | Analytis et al. |
| 2019/0343445 A1* | 11/2019 | Burnett .................. A61B 5/207 |
| 2019/0358387 A1 | 11/2019 | Elbadry et al. |
| 2019/0365308 A1 | 12/2019 | Laing et al. |
| 2019/0381223 A1 | 12/2019 | Culbert et al. |
| 2020/0022637 A1 | 1/2020 | Kurzrock et al. |
| 2020/0064172 A1 | 2/2020 | Tabaczewski et al. |
| 2020/0085378 A1 | 3/2020 | Burnett et al. |
| 2020/0121300 A1 | 4/2020 | Moore |
| 2020/0187863 A1 | 6/2020 | Tu et al. |
| 2020/0268302 A1 | 8/2020 | Oh |
| 2020/0268303 A1 | 8/2020 | Oliva |
| 2020/0289749 A1 | 9/2020 | Odashima et al. |
| 2020/0405524 A1 | 12/2020 | Gill |
| 2021/0054610 A1 | 2/2021 | Hall et al. |
| 2021/0077007 A1 | 3/2021 | Jouret et al. |
| 2021/0100533 A1 | 4/2021 | Seres et al. |
| 2021/0299353 A1 | 9/2021 | Mannu et al. |
| 2021/0361211 A1 | 11/2021 | Teramoto et al. |
| 2022/0018692 A1 | 1/2022 | Tourchak et al. |
| 2022/0026001 A1 | 1/2022 | Cheng et al. |
| 2022/0026261 A1 | 1/2022 | Funnell et al. |
| 2022/0079487 A1 | 3/2022 | Horiguchi et al. |
| 2022/0192564 A1 | 6/2022 | Kriscovich et al. |
| 2022/0192565 A1 | 6/2022 | Cheng et al. |
| 2022/0192566 A1 | 6/2022 | Cheng et al. |
| 2022/0193375 A1 | 6/2022 | Rehm et al. |
| 2022/0233120 A1 | 7/2022 | Beuret et al. |
| 2022/0296140 A1 | 9/2022 | Nguyen et al. |
| 2022/0330867 A1 | 10/2022 | Conley et al. |
| 2022/0386917 A1 | 12/2022 | Mann et al. |
| 2023/0019703 A1 | 1/2023 | Behzad et al. |
| 2023/0022547 A1 | 1/2023 | Cho et al. |
| 2023/0025333 A1 | 1/2023 | Patel et al. |
| 2023/0028966 A1 | 1/2023 | Franano |
| 2023/0035669 A1 | 2/2023 | Raja et al. |
| 2023/0040915 A1 | 2/2023 | Compton et al. |
| 2023/0058553 A1 | 2/2023 | Fallows et al. |
| 2023/0060232 A1 | 3/2023 | Patel et al. |
| 2023/0084476 A1 | 3/2023 | Robichaud et al. |
| 2023/0089041 A1 | 3/2023 | Handler |
| 2024/0081708 A1 | 3/2024 | Kelly et al. |
| 2024/0108268 A1 | 4/2024 | Woodard et al. |
| 2024/0252783 A1 | 8/2024 | Waitkus et al. |
| 2024/0347162 A1 | 10/2024 | Meese et al. |
| 2024/0360938 A1 | 10/2024 | Cheng et al. |
| 2024/0424186 A1 | 12/2024 | Justice et al. |
| 2025/0090066 A1 | 3/2025 | Tourchak |
| 2025/0120636 A1 | 4/2025 | Compton et al. |
| 2025/0205456 A1 | 6/2025 | Rehm et al. |
| 2025/0339073 A1 | 11/2025 | Cheng et al. |

FOREIGN PATENT DOCUMENTS

| CN | 200951235 Y | 9/2007 |
| CN | 201492414 U | 6/2010 |
| CN | 102647939 A | 8/2012 |
| CN | 103054559 B | 5/2015 |
| CN | 107952140 A | 4/2018 |
| CN | 109498013 A | 3/2019 |
| CN | 110859636 A | 3/2020 |
| CN | 112426156 A | 3/2021 |
| EP | 0342028 A2 | 11/1989 |
| ES | 2760470 T3 | 5/2020 |
| GB | 2437549 A | 10/2007 |
| GB | 2576743 A | 3/2020 |
| JP | S49-75171 A | 7/1974 |
| JP | S54-147066 A | 11/1979 |
| JP | S58-190719 A | 11/1983 |
| JP | S60-219517 A | 11/1985 |
| JP | H02057240 B2 | 12/1990 |
| JP | H08-271301 A | 10/1996 |
| JP | H10104041 A | 4/1998 |
| JP | 2007303982 A | 11/2007 |
| JP | 2008-524618 A | 7/2008 |
| JP | 2009-068959 A | 4/2009 |
| JP | 2010-121950 A | 6/2010 |
| JP | 2010-530978 A | 9/2010 |

(56) References Cited

FOREIGN PATENT DOCUMENTS

| JP | 2012-105947 A | 6/2012 | | |
|---|---|---|---|---|
| JP | 2012-225790 A | 11/2012 | | |
| JP | 2018108356 A | 7/2018 | | |
| KR | 20070115495 A | 12/2007 | | |
| NL | 2013740 A | 8/2016 | | |
| RU | 2615727 C2 | 4/2017 | | |
| WO | 1981003427 A1 | 12/1981 | | |
| WO | 2004045410 A1 | 6/2004 | | |
| WO | 2013013782 A2 | 1/2013 | | |
| WO | 20130178742 A1 | 12/2013 | | |
| WO | 2014043650 A2 | 3/2014 | | |
| WO | 2014105755 A1 | 7/2014 | | |
| WO | 2014108690 A1 | 7/2014 | | |
| WO | 2014135856 A1 | 9/2014 | | |
| WO | 2014145971 A2 | 9/2014 | | |
| WO | 2014151068 A2 | 9/2014 | | |
| WO | 201511402 A1 | 1/2015 | | |
| WO | 2015105916 A1 | 7/2015 | | |
| WO | 2015127390 A1 | 8/2015 | | |
| WO | 2015191125 A1 | 12/2015 | | |
| WO | 2016177901 A1 | 11/2016 | | |
| WO | 2017023794 A1 | 2/2017 | | |
| WO | 2018156624 A1 | 8/2018 | | |
| WO | 2019066357 A1 | 4/2019 | | |
| WO | 2019106675 A1 | 6/2019 | | |
| WO | WO-2019226697 A1 * | 11/2019 | ............ | A61M 27/00 |
| WO | 2020033752 A1 | 2/2020 | | |
| WO | 2020154370 A1 | 7/2020 | | |
| WO | 2020251893 A1 | 12/2020 | | |
| WO | 2022108589 A1 | 5/2022 | | |
| WO | 2022182794 A1 | 9/2022 | | |
| WO | 2023022895 A1 | 2/2023 | | |
| WO | 2023027871 A1 | 3/2023 | | |
| WO | 2023076067 A1 | 5/2023 | | |

OTHER PUBLICATIONS

PCT/US2019/033389 filed Nov. 26, 2020 Extended European Search Report dated Jun. 4, 2021.
U.S. Appl. No. 17/054,493, filed Nov. 10, 2020 Final Office Action dated Oct. 4, 2023.
U.S. Appl. No. 17/054,493, filed Nov. 10, 2020 Notice of Allowance dated Jan. 4, 2024.
U.S. Appl. No. 17/262,080, filed Jan. 21, 2021 Notice of Allowance dated Oct. 13, 2023.
U.S. Appl. No. 17/306,821, filed May 3, 2021 Advisory Action dated Oct. 3, 2023.
U.S. Appl. No. 17/373,546, filed Jul. 12, 2021 Non-Final Office Action dated Nov. 1, 2023.
U.S. Appl. No. 17/556,907, filed Dec. 20, 2021 Notice of Allowance dated Dec. 6, 2023.
Bard Medical, Criticore Disposables—Non I.C., 3 pages, www.bardmedical.com/products/patienl-monitoring-,ystems/criticore®-system/criticore®-disposables-non-ic/ Jan. 30, 2015.
Bard Medical, Criticore Infection Control Disposables, 3 pages, www.bardmedical.com/patienl-moniloring-,ystems/criticore®-system/criticore®-infection-control-disposables/ Jan. 30, 2015.
Bard Medical, Criticore Monitor, 11 pages, www.bardmedical.com/products/patient-monitoring-systems/criticore®--monitor/ Jan. 30, 2015.
Bard Medical, Urine Meiers, 3 pages, www.bardmedical.com/products/urological-drainage/urine-collection/urinemeters/ Jan. 30, 2015.
Biometrix, Urimetrix, 4 pages, www.biometrixmedical.com/Products/56/Urimetrix%E2%84%A2 Oct. 29, 2014.
Observe Medical, sippi, 3 pages, www.observemedical.com/products.html Oct. 29, 2014.
PCT/US19/33389 filed May 21, 2019 International Search Report and Written Opinion dated Aug. 2, 2019.
PCT/US20/61367 filed Nov. 19, 2020 International Search Report and Written Opinion dated Feb. 22, 2021.

PCT/US2016/044835 filed Jul. 20, 2016 International Search Report and Written Opinion dated Dec. 16, 2016.
PCT/US2019/045787 filed Aug. 8, 2019 International Preliminary Report on Patentability dated Feb. 16, 2021.
PCT/US2019/045787 filed Aug. 8, 2019 International Search Report and Written Opinion dated Oct. 2, 2019.
U.S. Appl. No. 15/748,107, filed Jan. 26, 2018 Final Office Action dated Dec. 23, 2020.
U.S. Appl. No. 15/748,107, filed Jan. 26, 2018 Final Office Action dated Feb. 7, 2022.
U.S. Appl. No. 15/748,107, filed Jan. 26, 2018 Non-Final Office Action dated Sep. 3, 2021.
U.S. Appl. No. 15/748,107, filed Jan. 26, 2018 Non-Final Office Action dated Sep. 4, 2020.
U.S. Appl. No. 15/748,107, filed Jan. 26, 2018 Notice of Allowance dated Dec. 12, 2022.
U.S. Appl. No. 17/054,493, filed Nov. 10, 2020 Final Office Action dated May 31, 2022.
U.S. Appl. No. 17/054,493, filed Nov. 10, 2020 Non-Final Office Action dated Jan. 27, 2023.
U.S. Appl. No. 17/054,493, filed Nov. 10, 2020 Non-Final Office Action dated Nov. 24, 2021.
U.S. Appl. No. 17/262,080, filed Jan. 21, 2021 Non-Final Office Action dated Apr. 6, 2023.
U.S. Appl. No. 17/306,821, filed May 3, 2021 Non-Final Office Action dated Jan. 10, 2023.
U.S. Appl. No. 17/373,535, filed Jul. 12, 2021 Non-Final Office Action dated Nov. 9, 2022.
U.S. Appl. No. 17/373,535, filed Jul. 12, 2021 Notice of Allowance dated Feb. 23, 2023.
U.S. Appl. No. 17/556,907, filed Dec. 20, 2021 Restriction Requirement dated May 12, 2023.
"Urocare Reusable Night Drain Bottle—Urinary Collection System" Aug. 13, 2020, HealthProductsForYou.com, <https://www.healthproductsforyou.com/p-urocare-reusable-night-drain-bottle-urinary-collection-system.html> retrieved from Archive.org (Year: 2020).
PCT/US2022/046920 filed Oct. 17, 2022 International Search Report and Written Opinion dated Feb. 20, 2023.
U.S. Appl. No. 17/373,546, filed Jul. 12, 2021 Notice of Allowance dated May 29, 2024.
U.S. Appl. No. 17/552,250, filed Dec. 15, 2021 Non-Final Office Action dated Sep. 19, 2024.
U.S. Appl. No. 17/556,931, filed Dec. 20, 2021 Advisory Action dated Dec. 6, 2024.
U.S. Appl. No. 17/556,931, filed Dec. 20, 2021 Final Office Action dated Oct. 1, 2024.
U.S. Appl. No. 17/560,079, filed Dec. 22, 2021 Notice of Allowance dated Oct. 29, 2024.
DFree Personal—Consumer Product Brochure, 2019.
DFree Pro Brochure 2019.
Leonhäuser, D et al., "Evaluation of electrical impedance tomography for determination of urinary bladder volume: comparison with standard ultrasound methods in healthy volunteers."—BioMed Engr On-line; 17:95; 2018.
Li, R., et al., "Design of a Noninvasive Bladder Urinary Volume Monitoring System Based on Bio-Impedance."—Engineering; vol. 5; pp. 321-325; 2013.
PCT/US2022/017574 filed Feb. 23, 2022 Internation Search Report and Written Opinion dated Jun. 8, 2022.
Reichmuth, M., et al., "A Non-invasive Wearable Bioimpedance System to Wirelessly Monitor Bladder Filling."—Dep. of Health Sciences and Technology—Department of Information Technology and Electrical Engineering ETH Zurich, Zurich, Switzerland—Conference Paper; Mar. 2020.
Schlebusch, T. et al., "Bladder volume estimation from electrical impedance tomography" Physiological Measurement, Institute of Physics, Bristol, GB. vol. 35 No. 9 Aug. 20, 2014. (Aug. 20, 2014).
SECA product catalog, https://us.secashop.com/products/seca-mbca/seca-mbca-514/5141321139, last accessed Sep. 11, 2020.
U.S. Appl. No. 17/262,080, filed Jan. 21, 2021 Final Office Action dated Sep. 11, 2023.

(56)                    References Cited

OTHER PUBLICATIONS

U.S. Appl. No. 17/306,821, filed May 3, 2021 Final Office Action dated Jul. 19, 2023.

U.S. Appl. No. 17/556,907, filed Dec. 20, 2021 Non-Final Office Action dated Aug. 17, 2023.

EP 20962628.2 filed May 31, 2023 Extended European Search Report dated Apr. 20, 2024.

PCT/US2022/039191 filed Aug. 2, 2022 International Search Report and Written Opinion dated Dec. 5, 2022.

PCT/US2022/039746 filed Aug. 8, 2022 International Search Report and Written Opinion dated Nov. 18, 2022.

U.S. Appl. No. 17/306,821, filed May 3, 2021 Notice of Allowance dated Apr. 23, 2024.

U.S. Appl. No. 17/373,546, filed Jul. 12, 2021 Notice of Allowance dated Mar. 7, 2024.

U.S. Appl. No. 17/556,931, filed Dec. 20, 2021 Non-Final Office Action dated Mar. 27, 2024.

U.S. Appl. No. 17/556,931, filed Dec. 20, 2021 Restriction Requirement dated Feb. 22, 2024.

"Volumetric Flow Rate", www.vcalc.com/wiki/JeffNolumetric+%28Fluid%29+Flow+Rate, accessed Jan. 9, 2025, created Mar. 8, 2018 (Year: 2018).

U.S. Appl. No. 17/552,250, filed Dec. 15, 2021 Final Office Action dated Feb. 11, 2025.

U.S. Appl. No. 17/556,931, filed Dec. 20, 2021 Notice of Allowance dated Mar. 18, 2025.

U.S. Appl. No. 17/587,938, filed Jan. 28, 2022 Restriction Requirement dated Jan. 22, 2025.

U.S. Appl. No. 17/833,682, filed Jun. 6, 2022 Non-Final Office Action dated Jan. 15, 2025.

U.S. Appl. No. 17/870,698, filed Jul. 21, 2022 Restriction Requirement dated Feb. 12, 2025.

U.S. Appl. No. 17/879,658, filed Aug. 2, 2022 Non-Final Office Action dated Dec. 30, 2024.

U.S. Appl. No. 17/893,435, filed Aug. 23, 2022 Non-Final Office Action dated Jan. 17, 2025.

U.S. Appl. No. 17/552,250, filed Dec. 15, 2021 Advisory Action dated May 8, 2025.

U.S. Appl. No. 17/552,250, filed Dec. 15, 2021 Notice of Allowance dated May 20, 2025.

U.S. Appl. No. 17/587,938, filed Jan. 28, 2022 Non-Final Office Action dated May 12, 2025.

U.S. Appl. No. 17/682,785, filed Feb. 28, 2022 Non-Final Office Action dated Jul. 16, 2025.

U.S. Appl. No. 17/682,785, filed Feb. 28, 2022 Restriction Requirement dated Apr. 2, 2025.

U.S. Appl. No. 17/833,682, filed Jun. 6, 2022 Final Office Action dated May 12, 2025.

U.S. Appl. No. 17/833,682, filed Jun. 6, 2022 Non-Final Office Action dated Sep. 15, 2025.

U.S. Appl. No. 17/863,223, filed Jul. 12, 2022 Non-Final Office Action dated Apr. 2, 2025.

U.S. Appl. No. 17/863,923, filed Jul. 13, 2022 Restriction Requirement dated May 21, 2025.

U.S. Appl. No. 17/870,698, filed Jul. 21, 2022 Final Office Action dated Jul. 29, 2025.

U.S. Appl. No. 17/870,698, filed Jul. 21, 2022 Non-Final Office Action dated Apr. 9, 2025.

U.S. Appl. No. 17/873,834, filed Jul. 26, 2022 Non-Final Office Action dated May 19, 2025.

U.S. Appl. No. 17/879,658, filed Aug. 2, 2022 Final Office Action dated May 14, 2025.

U.S. Appl. No. 17/883,507, filed Aug. 8, 2022 Non-Final Office Action dated Aug. 27, 2025.

U.S. Appl. No. 17/883,507, filed Aug. 8, 2022 Restriction Requirement dated May 19, 2025.

U.S. Appl. No. 17/893,435, filed Aug. 23, 2022 Notice of Allowance dated Jul. 11, 2025.

U.S. Appl. No. 17/941,941, filed Sep. 9, 2022 Non-Final Office Action dated Aug. 22, 2025.

U.S. Appl. No. 17/941,941, filed Sep. 9, 2022 Restriction Requirement dated May 28, 2025.

U.S. Appl. No. 18/278,167, filed Aug. 21, 2023 Non-Final Office Action dated Apr. 24, 2025.

U.S. Appl. No. 18/682,075, filed Feb. 7, 2024 Non-Final Office Action dated Jun. 18, 2025.

Weight Module Measuring Equipment, Hopper Weighing Module, www.web.archive.org/web/20210422161926/http://modul-ves.ru/catalog/bunkernye-vesy/vesovoy-modul-dlya-bunkera/, Apr. 22, 2021, accessed Sep. 10, 2025 (Year: 2021).

Weight Module Measuring Equipment, Hopper Weighing Module, www.web.archive.org/web/20210422161926/http://modul-ves.ru/catalog/bunkernye-vesy/vesovoy-modul-dlya-bunkera/, Apr. 22, 2021, translated via Google Translate, accessed Sep. 10, 2025 (Year:2025).

U.S. Appl. No. 17/863,223, filed Jul. 12, 2022 Final Office Action dated Sep. 24, 2025.

U.S. Appl. No. 17/863,923, filed Jul. 13, 2022 Non-Final Office Action dated Oct. 22, 2025.

U.S. Appl. No. 18/278,167, filed Aug. 21, 2023 Notice of Allowance dated Oct. 16, 2025.

* cited by examiner

DYNAMIC PRESSURE RESPONSE SYSTEM

This application is a U.S. national stage application of International Application No. PCT/US2020/061367, filed Nov. 19, 2020, which is incorporated by reference in its entirety into this application.

SUMMARY

Briefly summarized, embodiments disclosed herein are directed to a dynamic pressure response system for fully automated clearing of dependent loops from a fluid drainage system. Fluid drainage systems include a flexible drainage tube providing fluid communication with a collection container. The flexibility of the drainage tube can form sections of positive incline where drainage fluid can accumulate, also termed "dependent loops." Fluid pooling within these dependent loops can cause various complications. For example, urine pooling can be a source of catheter associated urinary tract infection ("CAUTI") causing agents such as bacteria, microbes, and the like. Hospital Acquired Infections ("HAI"), such as CAUTI, are detrimental to the patient, and also incur extra costs in treating these additional complications. Embodiments disclosed herein are directed to automatic clearing of these dependent loops while mitigating damage to the collection system and trauma to the patient.

Disclosed herein is a drainage system configured to drain a fluid from a body of a patient, the drainage system including a drainage tube defining a drainage lumen and configured to provide fluid communication between a catheter and a collection container, a connector providing pressurized air to the drainage lumen, the connector disposed proximate the catheter, a sensor disposed within the drainage lumen, and a controller logic configured to, i) detect a state of a drainage fluid disposed within the lumen, ii) modify a pressure level of the pressurized air provided by the connector, and iii) determine if the drainage lumen is clear of a drainage fluid.

In some embodiments, the drainage system further includes one or more solenoid valves communicatively coupled to the controller and configured to control one of a fluid communication between the catheter and the drainage lumen, or a fluid communication between the connector and the drainage lumen. The one or more solenoid valves configured to control fluid communication between the connector and the drainage lumen modifies a pressure level of pressurized air between 0% and 100%. The one or more solenoid valves configured to control fluid communication between the connector and the drainage lumen modifies a pressure level of pressurized air between a first pressurized air source and a second pressurized air source. The sensor is configured to detect one of an air pressure within the drainage lumen, or a state of the drainage fluid within the drainage lumen.

In some embodiments, the state of the drainage fluid includes one of a columnized fluid state, a mixed fluid state, or a no drainage fluid state. The controller logic is configured to detect one of an absolute pressure or a percentage change of pressure within the tube lumen. The percentage change of pressure is calculated by determining a moving average value of the absolute pressure values over time. The controller logic is configured to calculate a noise level to determine the state of the drainage fluid disposed within the lumen. A high noise level indicates a mixed fluid state and a low noise level with a pressure spike indicates a columnized fluid state. The noise level is calculated from an amplitude of the percentage change of pressure. The noise level is calculated by performing a Fast-Fourier-Transform (FFT) on the absolute fluid pressure values and determining the amplitude of the high frequency noise portion of the overall pressure signal. The controller logic reduces the pressure level of the pressurized air when the noise level drops below a threshold value. In some embodiments the catheter is configured to be disposed within a urethra to drain urine from a bladder of the patient.

Also disclosed is a method of draining a fluid from a patient including, detecting a presence of fluid within a lumen of a drainage tube, the drainage tube configured to provide fluid communication between a catheter and a collection container, determining a state of the fluid within the lumen, and providing one of a first pressure level or a second pressure level of pressurized air to the lumen.

In some embodiments, the method further includes closing a valve disposed between the catheter and the collection container before providing one of the first pressure level or the second pressure level of pressurized air to the connector. In some embodiments, providing one of a first pressure level or a second pressure level of pressurized air includes modifying a valve between a first open position to provide the first pressure level and a second open position to provide the second pressure level. In some embodiments, providing one of the first pressure level or the second pressure level of pressurized air includes modifying a pump between a first speed to provide the first pressure level and a second speed to provide the second pressure level. In some embodiments, the method further includes detecting an absence of fluid within the lumen and closing a valve, the valve configured to control providing the pressurized air to the lumen.

In some embodiments, the method further includes detecting pressure information from within the tube lumen and calculating a noise level from the pressure information to determine the state of the fluid within the lumen. In some embodiments calculating a noise level includes calculating one of a noise amplitude of the absolute fluid pressure values, a Fast-Fourier-Transformation of the absolute fluid pressure values to determine an amplitude of a high frequency noise portion of the overall pressure information, or an amplitude of a moving average of absolute fluid pressure values. In some embodiments, the method further includes comparing the noise level with a threshold value and modifying the pressurized air at the connector from the first pressure level to the second pressure level. In some embodiments the state of the fluid includes one of columnized fluid state or a mixed fluid state. In some embodiments, the catheter is configured to drain the fluid from a bladder of the patient and the fluid is urine.

Also disclosed is a drainage system including, a Foley catheter including at least one opening in a distal section, a urine collection container, and a drainage tube assembly fluidly coupling the Foley catheter and the urine collection container, the drainage tube assembly including, a drainage tube including a drainage lumen, a sensor disposed in the drainage lumen, a connector coupling the drainage tube to the Foley catheter, the connector including an inlet for receiving pressurized air, and a controller logic communicating with the drainage tube assembly configured to, i) detect a state of a drainage fluid disposed within the drainage lumen, ii) modify a pressure level of the pressurized air provided by the connector, and iii) determine if the drainage lumen is clear of a drainage fluid.

In some embodiments, the controller logic is configured to modify a valve disposed within the connector between a closed position and one or more open positions to modify a pressure level of the pressurized air. The controller logic is in communication with a pump configured to provide the pressurized air, the controller logic configured to modify the pressure level of the pressurized air by modifying the speed of the pump. The sensor is configured to detect a pressure of a fluid or a presence of a liquid within the drainage lumen. In some embodiments, detecting the state of the drainage fluid include measuring a pressure within the drainage lumen and calculating a noise level.

In some embodiments a high noise level indicates a mixed fluid state drainage fluid and the controller logic provides a high pressure level of pressurized air. The controller logic provides a low pressure level of pressurized air in response to a trigger, the trigger being predetermined time frame or an action. In some embodiments, calculating a noise level includes one of determining a percentage change in pressure values, determining a percentage change in a moving average of pressure values, or performing a Fast Fourier Transform of pressure values to detect an amplitude of a high frequency noise portion.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
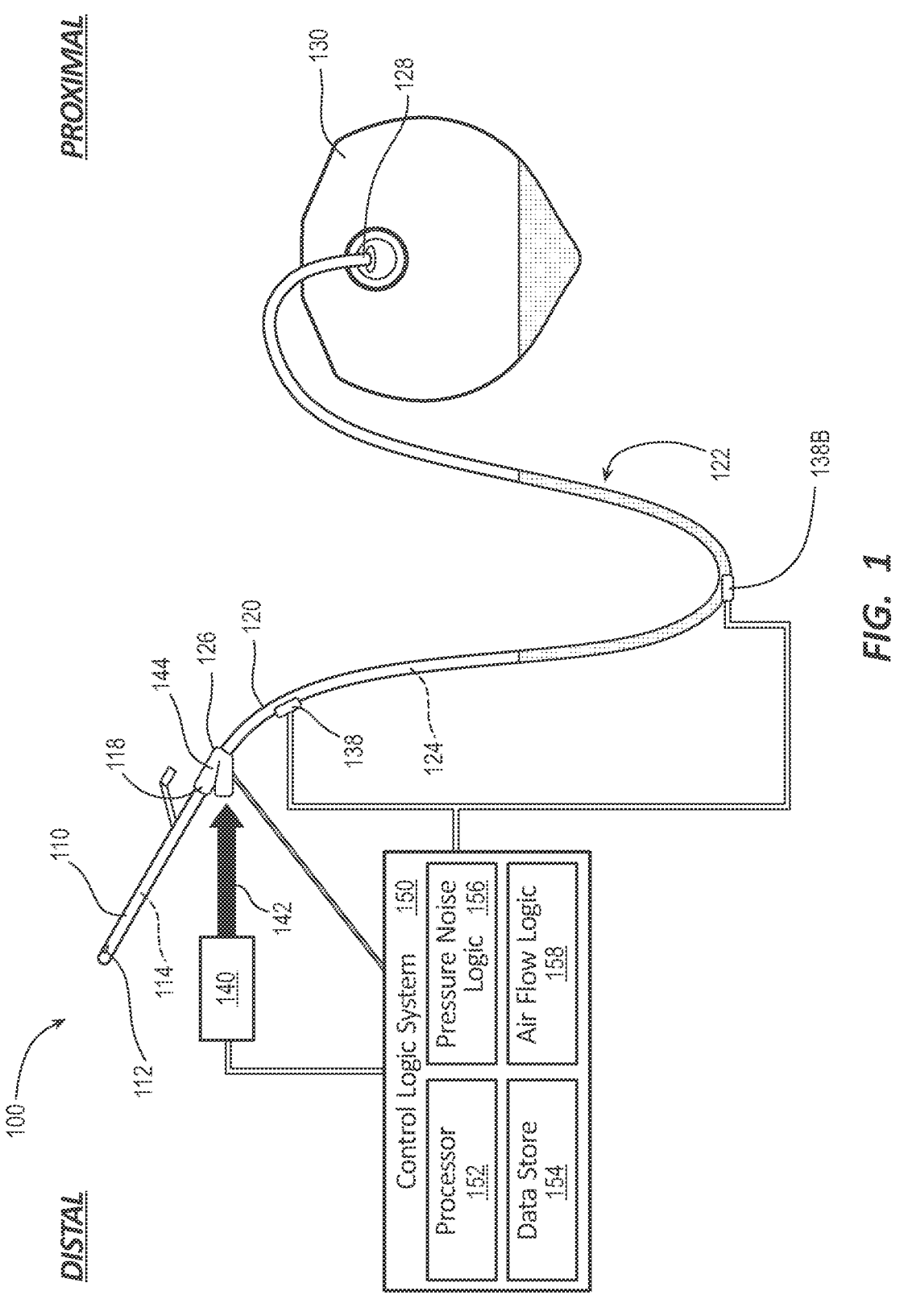
FIG. 1 shows an exemplary catheter and fluid collection system including a dynamic pressure response system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

To assist in the description of embodiments described herein, a longitudinal axis extends substantially parallel to an axial length of the catheter. A lateral axis extends normal to the longitudinal axis, and a transverse axis extends normal to both the longitudinal and lateral axes. Unless defined otherwise, all technical and scientific terms used herein have the same meaning as commonly understood by those of ordinary skill in the art.

In the following description, certain terminology is used to describe aspects of the invention. For example, in certain situations, the term "logic" is representative of hardware, firmware or software that is configured to perform one or more functions. As hardware, logic may include circuitry having data processing or storage functionality. Examples of such circuitry may include, but are not limited or restricted to a hardware processor (e.g., microprocessor with one or more processor cores, a digital signal processor, a programmable gate array, a microcontroller, an application specific integrated circuit "ASIC," etc.), a semiconductor memory, or combinatorial elements.

Alternatively, logic may be software, such as executable code in the form of an executable application, an Application Programming Interface (API), a subroutine, a function, a procedure, an applet, a servlet, a routine, source code, object code, a shared library/dynamic load library, or one or more instructions. The software may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; semiconductor memory; non-persistent storage such as volatile memory (e.g., any type of random access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the executable code may be stored in persistent storage.

The term "computing device" should be construed as electronics with the data processing capability and/or a capability of connecting to any type of network, such as a public network (e.g., Internet), a private network (e.g., a wireless data telecommunication network, a local area network "LAN", etc.), or a combination of networks. Examples of a computing device may include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

A "message" generally refers to information transmitted in one or more electrical signals that collectively represent electrically stored data in a prescribed format. Each message may be in the form of one or more packets, frames, HTTP-based transmissions, or any other series of bits having the prescribed format.

The term "computerized" generally represents that any corresponding operations are conducted by hardware in combination with software and/or firmware. As used herein, the term "fluid" can include a gas, liquid, or combination thereof.

Embodiments disclosed herein are directed to a dynamic pressure response drainage system including control logic configured to enable fully automated clearing of dependent loops from a drainage tube. The dynamic pressure response drainage system can automatically detect the presence of fluid within the drainage tube, determine a fluid state of the fluid within the drainage tube and modify a positive air pressure to clear the fluid from the drainage tube and into the collection container.

FIG. 1 shows an exemplary dynamic pressure response drainage system ("system") 100, which generally includes a catheter 110, a drainage tube ("tube") 120, a collection container ("container") 130, and a control logic system 150. Exemplary catheters 110 include indwelling catheters, Foley catheters, balloon catheters, peritoneal drainage catheters, or the like, and are configured to be inserted into an orifice within the body of a patient to drain a fluid therefrom. In an embodiment, the catheter 110 can be inserted through the urethra and into a bladder of a patient. The catheter 110 includes an eyelet 112 that provides fluid communication with a lumen 114 of the catheter 110, and is configured to drain a fluid, e.g. urine.

The tube 120 extends from a distal end 126 to a proximal end 128 to define an axial length, and defines a lumen 124. The distal end 126 of the tube 120 can be in fluid communication with a proximal 118 end of the catheter 110. The tube 120 provides fluid communication between the lumen 114 of the catheter 110 and the collection container 130. The tube 120 can be formed of rubber, plastic, polymer, silicone, or similar suitable material. The collection container 130 can include a rigid container, a flexible collection bag, or similar suitable container for receiving a fluid, e.g. urine, drained from the catheter 110.

As shown in FIG. 1, the flexibility of the drainage tube 120 can result in sections of the tube 120 providing a positive incline relative to the direction of fluid flow therethrough. These positive incline portions allow dependent loops 122 to form, which can lead to urine pooling within the tube 120. Urine pooling within the tube 120 can be a source of CAUTI causing agents, e.g. microbes, bacteria, etc. which can be detrimental to the patient. In an embodiment, a source of positive air pressure 140, e.g. a pump, or the like, can introduce a positive air pressure 142 into the tube lumen 124 at a point that is distal to the dependent loop 122. The positive air pressure 142 can urge the fluid through the tube lumen 124 and into the container 130. In an embodiment, the container 130 can include an outlet vent configured to release the positive air pressure within the system 100.

In an embodiment, the system 100 can include a connector piece ("connector") 144. The connector 144 can include a first inlet configured to couple with an outlet of the catheter 110 and provide fluid communication therebetween, and a second inlet configured to provide fluid communication with the source of positive air pressure 140. The first or the second inlet can be in fluid commination with an outlet of the connector piece 144. The connector outlet can be configured to couple with distal end 126 of the drainage tube 120 and provide fluid communication therebetween. The connector 144 can include one or more valves, e.g. solenoid valves or the like, configured to control a fluid flow between one of the first inlet, second inlet, or outlet of the connector 144. The valve can transition between a closed position and one or more open positions. The one or more open positions can be between 1% open and 100% open. Advantageously, the one or more open positions can provide different rates or pressures of fluid flow therethrough. As such the system 100 can modify the level of positive air pressure 142 entering the tube lumen 124, as described in more detail herein. Further, the system 100 can shut off a fluid flow between the tube lumen 124 and the catheter lumen 114 prior to introducing a positive air pressure 142 to the tube lumen 124 to prevent a distal flow of positive air pressure 142 into the patient. This can prevent trauma to the patient where, for example, the system 100 is activated while the catheter remains in position within the patient.

For example, the connector 144 can include a first valve disposed in the first inlet and configured to control a fluid flow between the catheter lumen 114 and the tube lumen 124. Further, the connector 144 can include a second valve disposed in the second inlet and configured to control a flow of positive air pressure 142 into the tube lumen 124. In an embodiment, the valve of the connector 144 can open to a first open position to provide a first pressure of positive air pressure 142 into the tube lumen 124. The valve can open to a second open position to provide a second pressure of positive air pressure 142, different from the first pressure. In an embodiment the valve of the connector 144 can close to provide no positive air pressure 142 to the tube lumen 124. It will be appreciated that the connector piece 144 can include different numbers or configurations of inlets, outlets, or valves and are contemplated to fall within the scope of the present invention.

In an embodiment, the pump 140 can operate at a first speed to provide a first pressure of positive air pressure 142, or at a second speed to provide a second pressure of positive air pressure 142, different from the first pressure. In an embodiment, the pump 140 can shut down to provide no positive air pressure 142 to the tube lumen 124. In an embodiment, the system 100 can include a first pump providing a first pressure of positive air pressure and a second pump providing a second pressure of positive air pressure different from the first pressure. The connector 144 can be configured to provide one of the first pressure from the first pump, or the second pressure from the second pump to the tube lumen 124. In an embodiment the valve(s) of the connector 144 can close to provide no positive air pressure 142 to the tube lumen 124. It will be appreciated that other numbers and configurations of connector valves 144, pumps 140, or the like, are also contemplated to fall within the scope of the present invention.

The system 100 can further include a dynamic control logic system ("control logic") 150. The control logic 150 can be communicatively coupled with one of the pump 140, the connector 144, or one or more sensors 138. The control logic 150 can include a processor 152, a data store 154, and one or more logic modules, for example a pressure noise logic module 156 and an air flow logic module 158.

In an embodiment, the pressure noise logic 156 can be communicatively coupled with one or more sensors 138 to detect an absolute pressure level within the tube lumen 124 and calculate a percentage change in pressure (%) to determine a "noise" level. In an embodiment, the air flow logic 158 can be configured to modify a positive air pressure 142 entering the tube lumen 124 between a low-flow and a high-flow. In an embodiment, the air flow logic 158 can be communicatively coupled with one of the pump 140 or the connector 144 to modify a speed of the pump 140 or one or more valves of the connector 144 to modify the positive air pressure 142 entering the system. The control logic 150 can be communicatively coupled with one or more sensors 138 configured to detect a pressure within the tube lumen 124, a state of fluid within the tube lumen 124, combinations thereof, or the like.

Figures 2A, 2B:
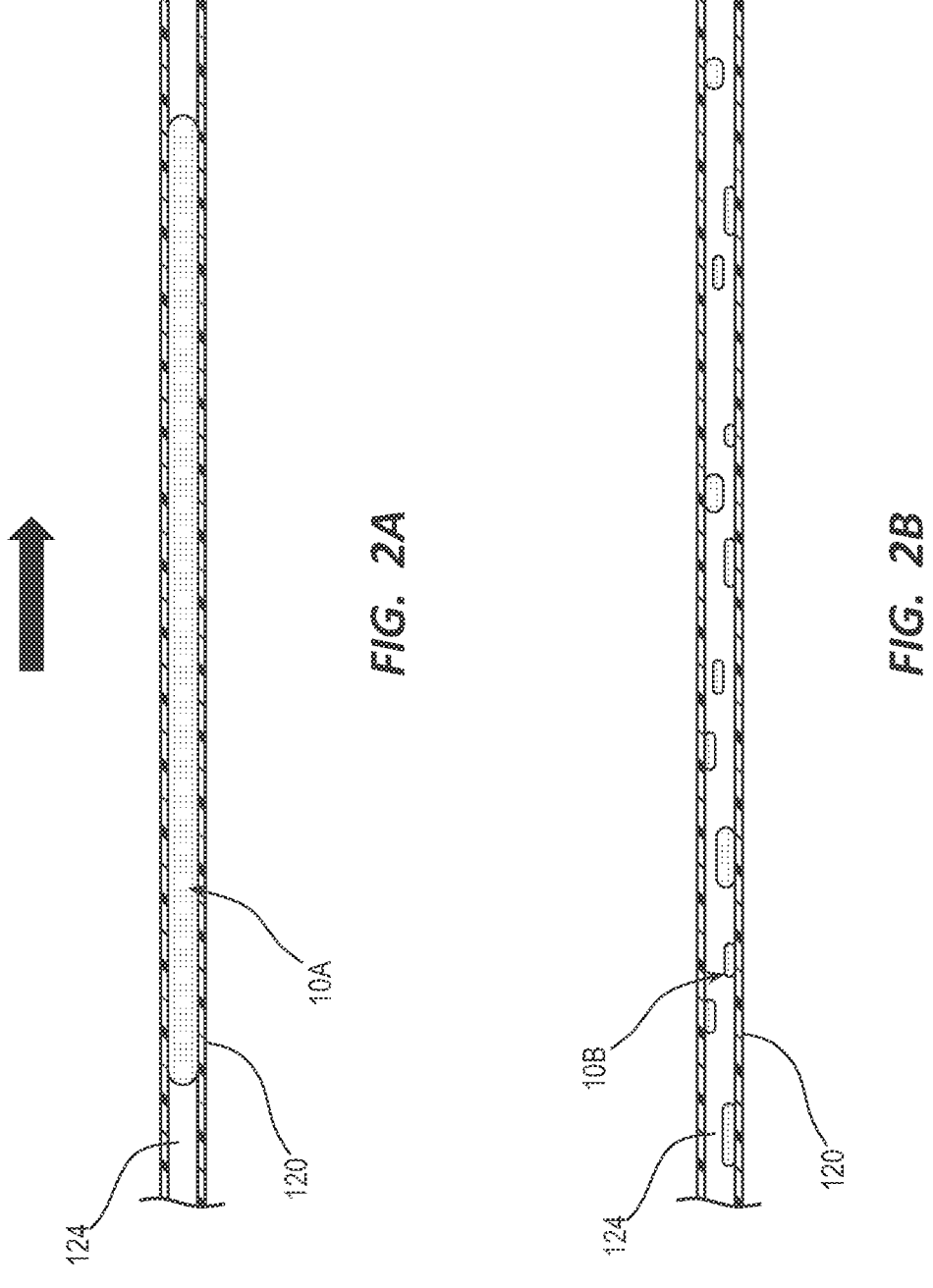
FIG. 2A shows an exemplary columnized fluid state within a drainage tube, in accordance with embodiments disclosed herein.
FIG. 2B shows an exemplary mixed fluid state within a drainage tube, in accordance with embodiments disclosed herein.

As shown in FIGS. 2A-2B, a fluid 10 disposed within the tube lumen 124 can be categorized into one of three states, a fully columnized fluid state, a mixed fluid state, or no fluid state. As shown in FIG. 2A, a fully columnized fluid state can occur when a liquid within the lumen 124 extends across the entire cross-sectional area of the tube lumen 124. As shown in FIG. 2B, a mixed fluid state can occur when a liquid within the lumen 124 does not extend across the entire cross-sectional area of the tube lumen 124 providing a mixture of gas and liquid within a given portion of tube lumen 124. A no fluid state occurs when little or no liquid, i.e. substantially negligible liquid, remains in the tube lumen 124.

As shown in FIG. 1, for a columnized fluid state, a relatively low static air pressure 142 will push a majority of the fluid within the tube lumen 124, from the dependent loop 122 into the collection container 130, independent of airflow rate. As the amount of liquid within the dependent loop 122 decreases, at a certain point the columnized fluid state will transition to a mixed fluid state where a relatively large positive air pressure 142 flow rate is needed to push the remaining liquid in the mixed flow state, into the collection container 130. As such, the rate of positive air pressure 142 entering the tube lumen 124 needs to change between a low-flow rate for columnized fluid state conditions and a high-flow rate for a mixed flow state conditions. It will be appreciated that high-flow rate and low-flow rate of positive air pressure 142 are exemplary and the system 100 can provide multiple flow rates, e.g. between 0% and 100% of maximum positive air pressure 142, to clear the tube lumen 124 depending on the amount of liquid within the tube, e.g. the number of the dependent loops 122, the column height of the dependent loop 122, the amount or proportion of liquid present in the columnized state or the mixed state, the axial length of tube 120, combinations thereof or the like. Advantageously, the system 100 can provide a positive air pressure 142 between 0% and 100% of maximum positive air pressure sufficient to clear the liquid from the tube lumen 124 without providing excessive positive air pressure that might cause trauma to the patient or damage to the system 100. Further, the system can modify the positive air pressure 142 between 0% and 100% to suit changing conditions within the tube lumen 124.

In an embodiment, the control logic 150 can measure pressure information within the tube lumen 124 and determine one of: the presence or absence of liquid within the tube lumen 124, the presence or absence of a dependent loop 122 within the tube lumen 124, the fluid state conditions, e.g. columnized or mixed state, within the tube lumen 124, a fluid pressure within the tube lumen 124, a fluid pressure spike, a fluid pressure drop, a transition between fluid states within the tube lumen 124, combination thereof, or the like. The control logic 150 can be configured to detect the presence of a dependent loop 122 within the tube lumen 124, modify the operation of one of the pump 140 or a valve system within the connector 144 to apply a positive air pressure 142 distally of the dependent loop 122, determine the presence of a columnized fluid state and apply a low-flow positive air pressure to urge the fluid through the tube lumen 124 and into the collection container 130. The control logic 150 can also determine a transition between the columnized fluid state and the mixed fluid state and modify one of the pump 140 or valve connector 144 to provide a high-flow positive air pressure. The control logic 150 can determine when the drainage tube 120 is sufficiently clear of liquid and either stop the positive air pressure 142 flow at the connector 144, or reduced the positive air pressure 142 flow to a low-flow rate.

It is important to note that a rapid detection of a change in fluid state between the columnized fluid state and the mixed fluid state, and a rapid change between the low-flow and high-flow positive air pressure 142 is important to avoid a large impulse force on the drainage system or the patient catheter 110. Detecting the change and reacting quickly can be important to avoid causing trauma to the patient or damaging the fluid collection system.

Figure 3:
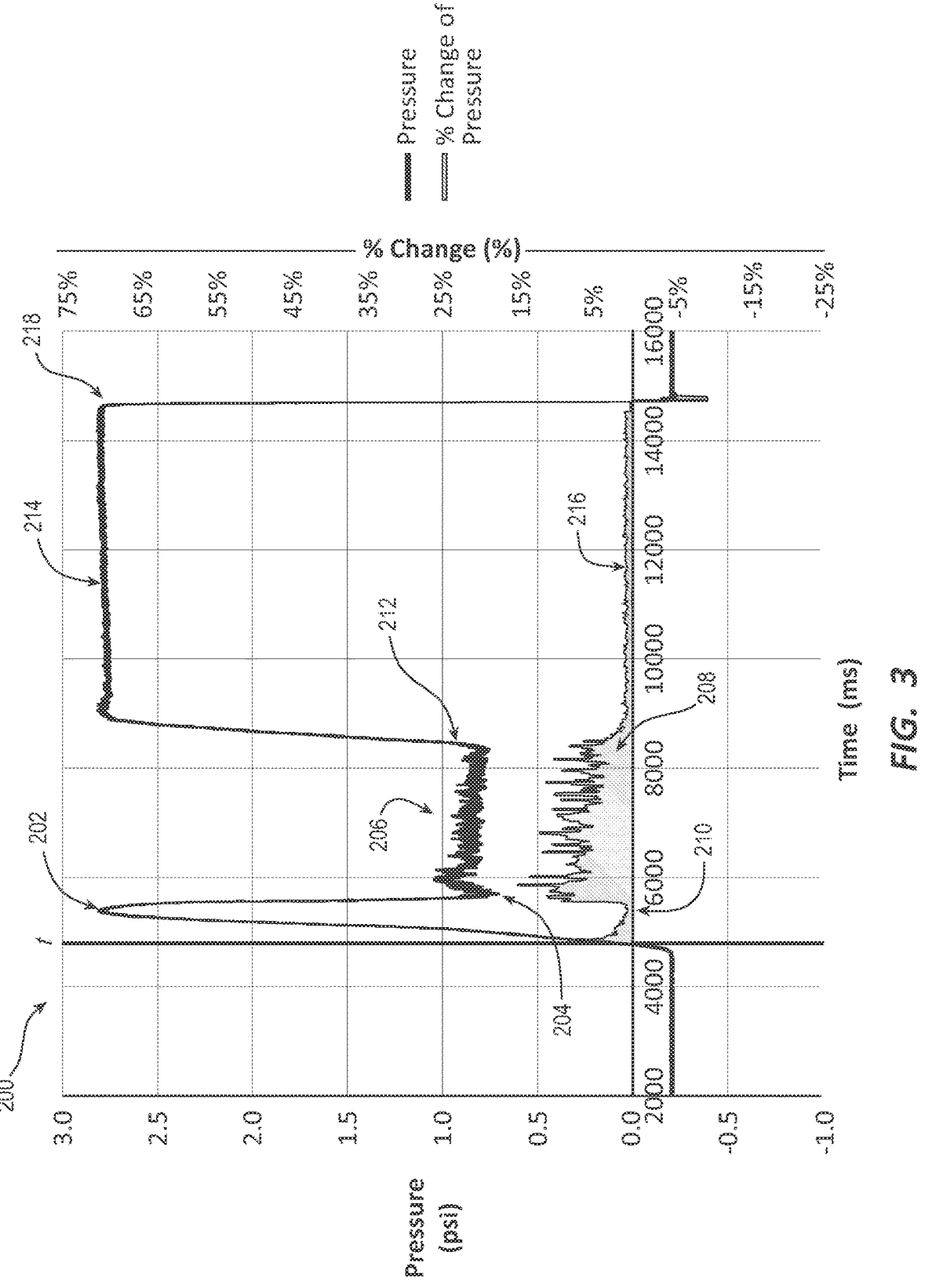
FIG. 3 shows a pressure chart for a fluid collection system including a dynamic pressure response system, in accordance with embodiments disclosed herein.

FIG. 3 shows a pressure chart 200 detailing exemplary pressure changes for the system 100 during operation. The pressure chart 200 shows an absolute fluid pressure ("Pressure" in psi) within the tube lumen 124 and a "Percentage change of pressure" (%). In an embodiment, the absolute fluid pressure can be detected by a pressure sensor, e.g. sensor 138, and can be a pressure of a gas, liquid, or combination thereof within the tube lumen 124. In an embodiment, the percentage change of pressure (%) can be calculated by determining a moving average of change in absolute fluid pressure values over time. Advantageously, the span of the moving average (e.g. average of a span of 2 data points, 5 data points, 10 data points, etc.) can be modified to provide different smoothing effects on the data and differentiate the change in noise levels between the different fluid states, as described herein.

In an embodiment, the control logic 150 can determine the fluid state within the tube lumen 124 based on the amount of "noise" in one of the absolute pressure values (psi) or percentage change in pressure (%) values over time. Where a relatively high level of "noise" can indicate a mixed fluid state. As noted, the columnized fluid state requires a relatively low static pressure to urge fluid through the tube lumen since the liquid creates a seal preventing the gas from passing the liquid. Such columnized fluid states can be detected based on a high absolute pressure increase and decrease over a relatively short time span (i.e. a pressure spike) and a low pressure noise (i.e. low cyclical change in pressure). As the liquid in the tube lumen 124 decreases the "seal" created by the columnized liquid can break, causing the columnized fluid to transition into mixed fluid state conditions. In mixed fluid state conditions, liquid droplets can break into smaller droplets or collapse into larger droplets, or columnize and decolumnize rapidly in a cyclical fashion. The positive air pressure 142 within the tube lumen 124 can compress against the cyclical columnizing and decolumnizing of the liquid which causes rapid cycling of pressure levels within the tube lumen 124 leading to a "noisy" pressure signal. In an embodiment, a level of "noise" can be calculated as a relatively high amplitude of percentage change (%) indicating a relatively noisy signal, and a relatively low amplitude of percentage change (%) can indicate a relatively stable signal.

In an embodiment, a value for the percentage change of pressure (%) can be calculated by performing a Fast-Fourier-Transform (FFT) on the absolute fluid pressure values and determining the amplitude of the high frequency noise portion of the overall pressure signal to determine a percentage change value (%). In an embodiment, a value for the level of noise can be calculated by performing a Fast-Fourier-Transform (FFT) on one of the absolute fluid pressure values or the percentage change of pressure (%) values and determining the amplitude of the high frequency noise portion of the signal to determine a "noise" level. As used herein, the "Fast-Fourier-Transform" can break a pressure signal, or percentage change value, down by frequency to isolate the amplitude of the high frequency noise associated with mixed flow states. The control logic 150 can determine the transition from the columnized fluid date to the mixed fluid state based on an increase in a "noise" level, or by comparing a "noise" level relative to a threshold value. The threshold value can be a predetermined value, or a dynamic value determined by the control logic system 150. The control logic 150 can then modify the positive air pressure 142 to a high-flow rate to clear the mixed fluid conditions.

For example, as shown in FIG. 3, a bolus (t) of fluid can enter the tube lumen 124 from the catheter 110 and can collect as a dependent loop 122. The fluid can columnize, blocking a low-flow positive air flow 142 from passing through the tube lumen 124 at the position of the dependent loop 122. In an embodiment, the control logic 150 can apply a constant positive air flow 142 to the tube lumen 124. This causes a pressure spike at 202 as the low-flow positive air pressure 142 builds and forces the columnized fluid through the tube lumen 124. In an embodiment, the control logic 150 can apply a positive air flow 142 to the tube lumen 124 in response to a trigger. The trigger can be a time based trigger or an action based trigger. In an embodiment, the control logic 150 can apply a positive air flow 142 after a given time frame has elapsed. In an embodiment, the control logic 150 can apply a positive air flow 142 in response to an action, e.g. an input from a user, the detection of a liquid within the drainage tube lumen 124, the detection of a dependent loop within the tube lumen 124, or the like.

In an embodiment, the control logic 150 can include a sensor, e.g. sensor 138B, configured to detect the presence or absence of fluid within the tube lumen 124. The control logic 150 can then modify one of the pump 140 or the valve(s) of the connector 144 to apply a low-flow positive air pressure 142 to the tube lumen 124 that compresses against the dependent loop 122 creating the pressure spike 202. Exemplary sensors 138B for detecting the presence of liquid or the presence of a dependent loop 122 can include pressure sensors, humidity sensors, capacitance sensors, or the like. Similarly, the sensor 138B can detect an absence of liquid within the tube lumen 124 to indicate to the controller logic 150 the tube lumen 124 is sufficiently clear of liquid. The positive air pressure 142 can push a fully columnized fluid through the tube lumen 124 and into the collection container 130 creating a rapid increase followed by a rapid decrease in pressure, with low-noise and high pressure amplitude indicating a pressure spike. The control logic 150 can detect the pressure spike to determine or confirm the presence of a columnized fluid state.

In an embodiment, a first valve at a first inlet between the catheter lumen 114 and the tube lumen 124 can be a one-way valve configured to allow a fluid flow to enter the tube lumen 124 from the catheter lumen 114 but prevent any reverse flow, from the tube lumen 124 to the catheter lumen 114. In an embodiment, the first valve can be a solenoid valve, the controller logic 150 can then shut the first valve at the first inlet before the providing a positive air pressure 142 to the tube lumen by way of the second inlet, either by opening the second valve or modifying the speed of the pump 140, or both, as described herein.

At 204, the low-flow positive air flow clears the columnized fluid from the tube lumen 124 and the fluid within the tube lumen 124 transitions from the columnized state to the mixed flow state. As such, the pressure within the lumen 124 drops sharply as the low-flow positive air pressure 142 can pass through the mixed state fluid within the tube lumen 124.

At 206, the remaining fluid within the tube lumen 124 in the mixed fluid conditions can break apart into smaller droplets or collapse into larger droplets, or columnize and decolumnize rapidly, in cyclical fashion, as the low-flow positive air pressure passes through the tube lumen 124. This high frequency, cyclical change fluid conditions can obstruct the tube lumen 124 differently causing high-frequency changes in pressure within the lumen 124 as the positive air pressure 142 passes through the mixed state fluid. These high-frequency changes in pressure create a "noisy" pressure signal, or gives a relatively high amplitude percentage change (%) reading 208, compared with the relative low percentage change (%) under columnized state conditions at 210.

The control logic 150 can detect the relatively high noise pressure signal and determine the transition from the columnized state to mixed flow state within the lumen 124. The control logic 150 can then modify the positive air flow 142 from a low-flow rate to a high flow rate at 212. The high-flow positive air pressure 142 can force the liquid of the mixed state fluid, through the tube lumen 124 and into the collection container 130. The high-flow positive air pressure 142 can provide a consistently high absolute pressure within the tube lumen 214, with relatively low noise, i.e. low amplitude percentage change (%) 216. At 218, the control logic 150 can then determine that the tube lumen 124 is sufficiently clear of liquid and can change the positive air flow from a high-flow rate to a low-flow rate or can stop the positive air flow altogether.

In an embodiment, the control logic 150 can monitor a percentage change (%) and can switch the positive air flow 142 from high-flow to low-flow, or shut off the positive air flow 142 when the noise level drops below a threshold value. In an embodiment, the control logic 150 can operate the high-flow positive air pressure 142 for a predetermined length of time at 214 to determine that the tube lumen 124 is clear. In an embodiment, the control logic 150 receive information from a sensor, e.g. sensor 138B, configured to detect when the tube lumen 124 is sufficiently clear of liquid, the control logic 150 can then reduce or shut off the positive air flow 142 when the tube lumen 124 is sufficiently clear of liquid. The sensor 138B can be a pressure sensor, a humidity sensor, capacitance sensor, or the like.

In an embodiment, the control logic 150 can maintain a continuous positive air pressure 142 through the tube lumen 124. In an embodiment, the control logic 150 can selectively start and a stop the positive air pressure 142 through the tube lumen 124 depending on the presence of fluid within the tube lumen 124 or the presence of dependent loops 122 within the tube lumen. In an embodiment, the control logic 150 can operate autonomously, requiring little or no input from a user, in order to urge fluid through the tube lumen 124 and clear dependent loops 122 therefrom.

Advantageously, the control logic 150 can automatically detect when fluid conditions within the tube lumen 124, transition between columnized and mixed flow conditions and can quickly modify the positive air pressure 142 between low-flow and high-flow. The timing of when the transition of fluid states and changes in flow rates can be important to avoid a large impulse forces on the drainage system and the patient catheter. Advantageously, the control logic 150 can constantly monitor fluid flow states within the tube lumen 124 and can react quickly (e.g. <1 sec.) to changing conditions.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A drainage system configured to drain a fluid from a body of a patient, the drainage system comprising:
   a drainage tube defining a drainage lumen and configured to provide fluid communication between a catheter and a collection container;
   a connector providing pressurized air to the drainage lumen, the connector disposed proximate the catheter;
   a sensor disposed within the drainage lumen; and
   a controller including logic and configured to:
      i) determine a state of a drainage fluid disposed within the drainage lumen by measuring a pressure within the drainage lumen and calculating a noise level;
      ii) modify a pressure level of the pressurized air provided by the connector; and
      iii) determine if the drainage lumen is clear of the drainage fluid.

2. The drainage system according to claim 1, further including one or more solenoid valves communicatively coupled to the controller and configured to control one of a fluid communication between the catheter and the drainage lumen, or a fluid communication between the connector and the drainage lumen.

3. The drainage system according to claim 2, wherein the one or more solenoid valves configured to control the fluid communication between the connector and the drainage lumen modifies the pressure level of pressurized air between 0% and 100%.

4. The drainage system according to claim 2, wherein the one or more solenoid valves configured to control the fluid communication between the connector and the drainage lumen modifies the pressure level of pressurized air between a first pressurized air source and a second pressurized air source.

5. The drainage system according to claim 1, wherein the sensor is configured to detect one of an air pressure within the drainage lumen, or the state of the drainage fluid within the drainage lumen.

6. The drainage system according to claim 1, wherein the state of the drainage fluid includes one of a columnized fluid state, a mixed fluid state, or a no drainage fluid state.

7. The drainage system according to claim 1, wherein measuring the pressure within the drainage lumen includes measuring one of an absolute pressure value or a percentage change of the pressure within the drainage lumen.

8. The drainage system according to claim 7, wherein the percentage change of pressure is calculated by determining a moving average value for a plurality of absolute pressure values over time.

9. The drainage system according to claim 1, wherein a high noise level indicates a mixed fluid state and a low noise level with a pressure spike indicates a columnized fluid state.

10. The drainage system according to claim 7, wherein the noise level is calculated from an amplitude of the percentage change of the pressure within the drainage lumen.

11. The drainage system according to claim 7, wherein the noise level is calculated by performing a Fast-Fourier-Transform (FFT) on a plurality of absolute pressure values and determining an amplitude of a high frequency noise portion of the FFT.

12. The drainage system according to claim 1, wherein the controller reduces the pressure level of the pressurized air when the noise level drops below a threshold value.

13. The drainage system according to claim 1, wherein the catheter is configured to be disposed within a urethra to drain urine from a bladder of the patient.

14. A drainage system, comprising:
   a Foley catheter including at least one opening in a distal section;
   a urine collection container;
   a drainage tube assembly fluidly coupling the Foley catheter and the urine collection container, the drainage tube assembly comprising:
      a drainage tube including a drainage lumen;
      a sensor disposed in the drainage lumen; and
      a connector coupling the drainage tube to the Foley catheter, the connector including an inlet for receiving pressurized air; and
   a controller logic communicating with the drainage tube assembly configured to:
      i) determine a state of a drainage fluid disposed within the drainage lumen by measuring a pressure within the drainage lumen and calculating a noise level;
      ii) modify a pressure level of the pressurized air provided by the connector; and
      iii) determine if the drainage lumen is clear of the drainage fluid.

15. The drainage system according to claim 14, wherein the controller logic is configured to modify a valve disposed within the connector between a closed position and one or more open positions to modify the pressure level of the pressurized air.

16. The drainage system according to claim 14, wherein the controller logic is in communication with a pump configured to provide the pressurized air, the controller logic configured to modify the pressure level of the pressurized air by modifying a speed of the pump.

17. The drainage system according to claim 14, wherein the sensor is configured to detect a pressure of a fluid or a presence of a liquid within the drainage lumen.

18. The drainage system according to claim 14, wherein a high noise level indicates a mixed fluid state drainage fluid and the controller logic provides a high pressure level of pressurized air.

19. The drainage system according to claim 18, wherein the controller logic provides a low positive pressure level of pressurized air, relative to the high pressure level of pressurized air, in response to a trigger, the trigger being a predetermined time frame or an action.

20. The drainage system according to claim 14, wherein calculating the noise level includes one of determining a percentage change in pressure values, determining a percentage change in a moving average of pressure values, or performing a Fast Fourier Transform of pressure values to detect an amplitude of a high frequency noise portion.

* * * * *